United States Patent [19]

Cornell

[11] Patent Number: 4,704,303

[45] Date of Patent: Nov. 3, 1987

[54] NAIL EXTENSION COMPOSITION

[76] Inventor: John A. Cornell, 1306 Birmingham Rd., West Chester, Pa. 19382

[21] Appl. No.: 898,233

[22] Filed: Aug. 20, 1986

[51] Int. Cl.$^4$ .............................................. B05D 3/06
[52] U.S. Cl. ..................................... 427/53.1; 424/61; 427/54.1; 522/90; 522/96
[58] Field of Search ................ 522/90, 96; 427/44, 427/53.1, 54.1; 424/61

[56] References Cited

U.S. PATENT DOCUMENTS

| | | | |
|---|---|---|---|
| 4,216,267 | 8/1980 | Lorenz et al. | 522/90 |
| 4,512,910 | 4/1985 | Schmiole | 522/90 |
| 4,533,445 | 8/1985 | Orio | 522/96 |
| 4,544,625 | 10/1985 | Ishimaru et al. | 430/270 |
| 4,596,260 | 6/1986 | Giuliano | 424/61 |
| 4,607,084 | 8/1986 | Morris | 522/90 |

Primary Examiner—John H. Newsome
Attorney, Agent, or Firm—Cushman, Darby & Cushman

[57] ABSTRACT

A combination of a human nail and an artificial nail cover are coated by (1) first applying to the surface of the combination a monomeric aliphatic or cycloaliphatic hydrocarbon urethane dimethacrylate, a photo cure system and methacrylic acid and then curing in the visible light range and then applying a composition of the monomeric urethane or methacrylate, a polymeric aliphatic of cycloaliphatic hydrocarbon urethane acrylate methacrylate, a low viscosity polyglycol dimethacrylate and a photo cure system and curing in the visible range.

14 Claims, No Drawings

NAIL EXTENSION COMPOSITION

BACKGROUND OF THE INVENTION

The present invention relates to a composition and method for coating a combination of a natural nail, e.g., a human fingernail and an artificial nail.

Prior coating systems have usually required mixing powder-liquid giving an uneven porous surface which is generally over-applied and filed off. The systems are heat cured, the set time depends on temperature and cannot be controlled. The monomers employed are odoriferous, hard on the skin, flammable, and volatile. The trapping of moisture under the coating leading to easy tearing of the natural nail and fungal growth.

SUMMARY OF THE INVENTION

The invention is designed to apply an overall coating to a combination natural nail, e.g., a fingernail and an artificial nail extension. The natural nail and artificial nail can be secured together in any fashion known in the art, e.g., using an adhesive such as cyanoacrylate adhesive, e.g., a butyl cyanoacrylate adhesive or using a system such as that disclosed and claimed in Ferraro U.S. Pat. No. 4,511,608, the entire disclosure of which is hereby incorporated by reference and relied upon.

The nail extension coating composition of the present invention is of the photocuring type. No mixing is required, there is a smoother application, there are no bubbles and no time limit to the application. The material can be wiped off and reapplied if necessary and it behaves similar to nail polish.

Only a single container is required. Layers can be added sequentially, if desired, and cured to each other. Touch up is easy.

There have been proposed photo curable liquid nail lacquers and base coats in the past, e.g., see Rosenberg U.S. Pat. No. 3,896,014 and Rosenberg U.S. Pat. No. 3,928,113. The entire disclosures of both Rosenberg patents are hereby incorporated by reference and relied upon. The Rosenberg patents both require the use of polythiols.

The recently issued Giuliano U.S. Pat. No. 4,596,260 is directed to a process of applying a coating of an organic solvent-free photocurable liquid composition curable upon exposure to actinic radiation to the surface of a combination of preformed artificial nail tip adhered to a natural nail tip, and then exposing the applied composition to actinic radiation to initiate curing. However, there is no specific mention of curing in the visible light range and emphasis is placed on UV curing.

Giuliano both in the patent on col. 5, lines 40–46, and in its file history refers to low molecular weight urethane oligomers containing molecular weights of about 600 to about 8000 and indicates that the acrylated urethanes are preferred. No mention is made of the use of monomeric urethanes rather than oligomeric urethanes. The entire disclosure of Giuliano is hereby incorporated by reference and relied upon.

Ishimaru U.S. Pat. No. 4,544,625 discloses a photosensitive resin composition for forming a solder mask which include a urethane diacrylate or methacrylate made from trimethylhexylene diisocyanate and an acrylic or methacrylic monoester of a dihydric alcohol having 1 to 8 carbon atoms. There is also present a linear polymeric compound having a glass transition temperature of 40° to 150° C., a sensitizer and an acrylic or methacrylic phosphate. The entire disclosure of Ishimaru is hereby incorporated by reference and relied upon.

Dart U.S. Pat. No. 4,071,424 discloses a photopolymerizable composition comprising at least one polymerizable ethylenically unsaturated material and a photosensitive catalyst comprising a keto compound and a reducing agent. Dart can employ as the unsaturated material the reaction product of a hydroxyalkyl acrylate or methacrylate with an isocyanate ended adduct of a diol and a diisocyanate and specifically mentions the reaction product of hydroxyethyl methacrylate and an isocyanate-ended adduct of 4,4'-diphenyl methane diisocyanate and oxypropylated bisphenol-A. No mention is made of coating nails. The entire disclosure of Dart is hereby incorporated by reference and relied upon.

Denyer U.S. Pat. No. 4,457,818 discloses a liquid dental composition which comprises a prepolymer made from the reaction of hexamethylene diisocyanate and propoxylated bisphenol A and hydroxypropyl methacrylate, a glycol dimethacrylate, dimethylaminoethyl methacrylate and camphorquinone.

It has now been found that a particularly useful nail extension coating can be prepared from a composition comprising, consisting of, or consisting essentially of:

(a) a monomeric urethane diacrylate or more preferably a urethane dimethacrylate having a molecular weight range of 250–500 and a viscosity of 5000 to 30,000. The diisocyanate employed to form the polyurethane is an unsubstituted aliphatic or cycloaliphatic hydrocarbon diisocyanate, e.g., heptyl diisocyanate (e.g., 3-methylhexyldiisocyanate), 2,2,4-trimethylhexyl diisocyanate, hexyl-diisocyanate-1,6 and 3-isocyanomethyl-3,5,5-trimethyl cyclohexyl isocyanate. The preferred urethane diisocyanate is made from 3-methylhexyldiisocyanate and hydroxyethyl methacrylate. It is available commercially as RM-3 or as MHOROMER 6661-0(Rhom Tech. Inc). Chemically its name is 7,7,9-trimethyl-4,13-dioxo-3,14-dioxa-5,12-diazahexadecan-1,16-diol-dimethacrylate. The urethane dimethacrylate gives toughness, adhesion, good aging properties, ease of curing, surface hardness, easy finishing and moisture transmission. They also aid in adding the other components and impart better flow properties;

(b) a toughness modifier (polymeric) a higher molecular weight urethane acrylate or dimethacrylate, molecular weight range 800–1600. This gives adhesion, toughness, and viscosity control. Suitable aliphatic or cycloaliphatic urethane acrylate polymers are C-9500 (molecular weight 900), C-9501 (molecular weight 1200), and C-9505 (molecular weight 1600) a 2-hydroxyethyl ester acrylate polymer with 1,1'-methylene bis[4-isocyanato-cyclohexane] and 2-hydroxy propanol having the formula $(C_5H_8O_3C_{15}H_{22}N_2O_2(C_6H_{10}O_2))_x$. These compounds are di and trifunctional polyester polyol based cycloaliphatic urethane acrylates;

(c) a low viscosity polyglycol dimethacrylate. This gives viscosity control and high moisture transmission. They can have a molecular weight range of 286–750 and a viscosity of 7–130 cps. Typical examples are triethylene glycol dimethacrylate, tetraethylene glycol dimethacrylate, polyethylene glycol 200 dimethacrylate, polyethylene glycol 400 dimethacrylate, and polyethylene glycol 600 dimethacrylate (e.g., SR-252);

(d) a photocure system which cures in the visible light range, e.g., nanometers 400–500. The system will normally cure in 30 seconds or less with light sources such as a Sun lamp or in 15 minutes in sunlight. Typical suitable light sources are shown in the Rosenberg patents and the Dart patent. Illustrative photocure systems include sensitizers such as camphoquinone, 4,4'-dimethoxy benzil, 4,4'-dimethyl benzil and benzil. Typical amine promoters includes dimethyl aminoethyl methacrylate, dimethyl p-toluidine and Michler's ketone. There can be used any of the other sensitizers and promoters shown in the Dart patent, for example. The ratio of sensitizer to promoter is usually 1:1 on a molar basis but this can be varied. The amine promoter can be omitted but is preferably employed. Based on the ethylenically unsaturated material, the photosensitizer can be present in an amount of 0.001% to 10% by weight, usually 0.1 to 7% by weight and most preferably 0.5 to 5% by weight. The promoter can be present in the same weight range and is usually present in an amount of 0.5 to 5% by weight of the ethylenically unsaturated material;

(e) optionally, there can be present various additives such as pigments, dyes, inhibitors, fillers, fibers (to increase resistance to breakage), thixotropic agents, etc.

While Giuliano prefers the use of acrylated urethane oligomers it is essential in the present invention that there be employed urethane dimethacrylate monomers. The urethane diacrylate monomers are considerably more toxic than the urethane dimethacrylate monomers. It has also been found that while the monomeric urethane dimethacrylates of the invention do not cure as well as the monomeric-urethanediacrylates using UV light the monomeric urethane dimethacrylates do cure as well as the urethane diacrylates using visible light.

The ratio of component (a) to component (b) can be from 95 to 5% by weight (a) to 70 to 30% by weight (b). Component (c) can be 5 to 30% of the total of (a), (b), and (c).

As a bonding agent to the natural nail and to the nail extension, there can be used a composition comprising:

(a) urethane dimethacrylate of the type used in the coating and (b) an adhesive to keratin. One suitable type is methacrylic acid which appears to bond to the fingernail and will copolymerize with the urethane dimethacrylate using a photocure system. There may also be present a polyethylene glycol dimethacrylate.

Optionally, there can be applied over the coating a top coating of a urethane dimethacrylate having a molecular weight of 250-500 and viscosity range of 5000 to 3000 cps. This can be the same type of urethane dimethacrylate as set forth above for the coating.

DETAILED DESCRIPTION

A typical procedure for use by a beautician in preparing a fingernail according to the invention is as follows:

Place one small bead of an adhesive, e.g, a butyl cyanoacrylate adhesive on the thin contact-area on the back side of the artificial nail tip. Place another very small bead of the adhesive composition on the natural nail plate near the free edge. Spread the bonding composition gently with the tip to completely coat the entire free edge with adhesive.

Slide the tip on the edge of the nail until it is completely butted against the "stop" or ridge on the back side of the tip. Once the "stop" is placed on the underside, press firmly down onto the nail plate with the tip to gradually squeeze all air bubbles from the contact point. This will guarantee total encasement of the natural nail in the tip stop.

Cut the tip with a cuticle scissor to the desired length and buff the contact area to the natural nail.

Apply a thin coat of the bonding composition on the entire nail surface: natural nail and artificial nail. Apply enough to just wet the surface. Drop a small bead of the bonding composition on the middle of a nail. Brush thin. Apply the bonding composition up to, but not on the cuticle of the nail plate and allow a small hairthin area to remain uncovered on the nail plate around the cuticle area. This will prevent contact of the coating composition with the skin, eliminating the possibility of lifting.

Then there is applied the coating composition. Usually there are used three thin coats for thin or weak natural nails, two thin coats for normal to strong nails. The polymethacrylates in the coating composition give strength to the product and crosslink to prevent yellowing and softening in solvents.

One or two beads of the coating composition is dropped in the middle of the nail plate (use one bead for a small plate, one to two medium beads for a medium plate, and two good size beads for a large plate).

Using a brush gently spread the coating composition (in the form of a gel) over the entire nail plate and tip extension. Leave a thin space around the nail plate so the composition does not touch the cuticle. Do not overbrush since too much brushing creates bubbles on the surface, which prevents the desired gloss.

Let the nail set for 15–30 seconds before curing. This will allow the gel to self-level. One finger should be cured at a time. (Usually the thumb is coated first). Re-coat the other fingernails while each one is curing until the desired number of coats are achieved.

Cure the nail with a "Solar Beam" lamp (or any other source of visible light in the 400–500 nanometer region) for 20 seconds. Apply another thin coat of the gel and cure again for 20 seconds. A final cure is given for 20 seconds.

In the following formulations, all parts are by weight.

| Material | Coating Compositions | | |
| --- | --- | --- | --- |
|  | 1 | 2 | 3 |
| RM3 | 1620 | 1630 | 1600 |
| C9505 | 200 | 200 | 200 |
| SR 252 | 180 | 170 | 200 |
| Camphoquinone | 2.7 | 2.7 | 2.7 |
| Dimethylaminoethyl methacrylate | 5.0 | 5.0 | 5.0 |

| Material | Bonding Composition | | |
| --- | --- | --- | --- |
|  | 4 | 5 | 6 |
| RM3 | 1640 | 444 | 222 |
| C9505 | — | 222 | 222 |
| Polyethylene glycol 200 dimethacrylate | — | 934 | 1110 |
| Methacrylic acid | 360 | 400 | 442 |
| Camphoquinone | 2.7 | 2.7 | 2.7 |
| Dimethylaminoethyl methacrylate | 5.0 | 5.0 | 5.0 |

What is claimed is:

1. A composition suitable for coating nails comprising (a) an aliphatic or cycloaliphatic hydrocarbon urethane diacrylate or dimethacrylate having a molecular weight of 250 to 500 and a viscosity of 5,000 to 30,000 cps, (b) a polymeric aliphatic or cycloaliphatic hydrocarbon urethane diacrylate or dimethacrylate having a molecular weight of 800 to 1600, (c) a low viscosity polyglycol dimethacrylate having a molecular weight of 286 to 750 and (d) a photocure system which cures in the visible light range.

2. A composition according to claim 1 wherein (a) is 7,7,9-trimethyl-4,13-dioxo-3,14-dioxa-5,12-diazahexadecan-1,16-diol-dimethacrylate.

3. A composition according to claim 2 consisting essentially of (a), (b), (c), and (d).

4. A composition according to claim 1 consisting essentially of (a), (b), (c), and (d).

5. A method of coating a combination of a human nail and an artificial nail covering comprising applying the composition of claim 1 over the surface of the combination of nails and then curing the composition in the visible light range.

6. A method of coating a combination of a human nail and an artificial nail covering comprising applying the composition of claim 2 over the surface of the combination of nails and then curing the composition in the visible light range.

7. A method of coating a combination of a human nail and an artificial nail cover comprising (1) first applying to the surface of the combination of nails a bonding composition comprising (a) a monomeric aliphatic or cycloaliphatic hydrocarbon urethane dimethacrylate, (d) a photocure system which cures in the visible light range and (e) methacrylic acid as a bonding agent, curing the bonding composition and then (2) applying over the bonding composition the coating composition of claim 1 and then curing the coating composition in the visible light range.

8. A method according to claim 7 where (a) is 7,7,9-trimethyl-4,13-dioxo-3,14-dioxa-5,12-diazahexadecan-1,16-diol-dimethacrylate.

9. A method according to claim 7 wherein the bonding composition also includes (b) a polymeric aliphatic or cycloaliphatic hydrocarbon urethane diacrylate or dimethacrylate having a molecular weight of 800 to 1600 and (c) is a low viscosity polyglycol dimethacrylate having a molecular weight range of 286 to 750.

10. A method according to claim 9 where (a) is the reaction production of heptyl diisocyanate and hydroxyethyl methacrylate.

11. A composition suitable for bonding to a nail comprising (a) a monomeric aliphatic or cycloaliphatic hydrocarbon urethane dimethacrylate have a molecular weight of 250 to 500 and a viscosity of 5,000 to 30,000, (d) a photocure system which cures in the visible light range, and (e) methacrylic acid.

12. A composition according to claim 11 also including (b) a polymeric aliphatic or cycloaliphatic hydrocarbon urethane diacrylate or dimethacrylate having a molecular weight of 800 to 1600 and (c) a low viscosity polyglycol dimethacrylate having a molecular weight of 286 to 750.

13. A composition according to claim 12 wherein (a) is 7,7,9-trimethyl-4,13-dioxo-3,14-dioxa-5,12-diazahexadecan-1,16-diol-dimethacrylate.

14. A composition according to claim 11 wherein (a) is 7,7,9-trimethyl-4,13-dioxo-3,14-dioxa-5,12-diazahexadecan-1,16-diol-dimethacrylate.

* * * * *